United States Patent [19]

Barner et al.

[11] Patent Number: 5,057,530

[45] Date of Patent: Oct. 15, 1991

[54] GLYCEROL DERIVATIVES

[75] Inventors: Richard Barner, Witterswil; Kaspar Burri, Rheinfelden, both of Switzerland; Jean-Marie Cassal, Mulhouse, France; Paul Hadvary, Biel-Benken, Switzerland; Georges Hirth, Huningue, France; Klaus Müller, Münchenstein, Switzerland

[73] Assignee: Hoffmann-La Roche Inc., Nutley, N.J.

[21] Appl. No.: 354,186

[22] Filed: May 19, 1989

Related U.S. Application Data

[62] Division of Ser. No. 871,185, Jun. 5, 1986, Pat. No. 4,863,941.

[30] Foreign Application Priority Data

Jun. 18, 1985 [CH] Switzerland ............... 2567/85

[51] Int. Cl.[5] ............... A61K 31/415; A61K 31/425
[52] U.S. Cl. ............... 514/365; 514/247; 514/277; 514/307; 514/311; 514/315; 514/374; 514/378; 514/399
[58] Field of Search ............... 514/365, 399, 315, 247, 514/277, 307, 311, 374, 378

[56] References Cited

U.S. PATENT DOCUMENTS 4,731,373 3/1988 Barner et al. ............... 514/365

FOREIGN PATENT DOCUMENTS

| | | |
|---|---|---|
| 70433A1 | 1/1983 | European Pat. Off. . |
| 94186A1 | 11/1983 | European Pat. Off. . |
| 94586A2 | 11/1983 | European Pat. Off. . |
| 109255A2 | 5/1984 | European Pat. Off. . |
| 138558A2 | 4/1985 | European Pat. Off. . |
| 138559A2 | 4/1985 | European Pat. Off. . |
| 142333A2 | 5/1985 | European Pat. Off. . |
| 146258 | 6/1985 | European Pat. Off. ............ 548/181 |
| 157609 | 9/1985 | European Pat. Off. ............ 548/181 |
| 157609A | 10/1985 | European Pat. Off. . |
| 3212387A1 | 10/1983 | Fed. Rep. of Germany . |
| 8335116 | 3/1983 | Japan . |
| 83154512 | 9/1983 | Japan . |
| 8431738 | 2/1984 | Japan . |
| 8335194 | 3/1984 | Japan . |
| 854196 | 1/1985 | Japan . |
| 85104066 | 6/1985 | Japan . |

*Primary Examiner*—Robert Gerstl
*Attorney, Agent, or Firm*—George M. Gould; Bernard S. Leon; Ellen Ciambrone Coletti

[57] ABSTRACT

Glycerol derivatives of the formula

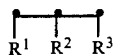

wherein one of the residues $R^1$, $R^2$ and $R^3$ is a group U of the formula $OY^1$ or $-X^1-CO-(A^1)_n-Z^1$, another residue is a group V of the formula $OY^2$ or $-X^2-CO-(A^2)_p-Z^2$, and the remaining residue is a group W of the formula $-X^3T-(C_{2-6}\text{-alkylene})-N^+R$ $A^-$ in which one of $X^1$, $X^2$ and $X^3$ is oxygen or $NQ^1$ and the other two are oxygen and the remaining symbols have the significance given below, and their hydrates are described and are prepared by introducing or generating the residues $R^1$, $R^2$ and $R^3$ in corresponding glycerol derivatives.

The compounds of formula I are active as inhibitors of blood platelet activating factor or as inhibitors of the growth of tumors.

5 Claims, No Drawings

GLYCEROL DERIVATIVES

This is a division of application Ser. No. 06/871,185 filed June 5, 1986, now U.S. Pat. No. 4,863,941.

BRIEF SUMMARY OF THE INVENTION

The present invention relates to glycerol derivatives, a process for their preparation and medicaments based on these glycerol derivatives.

The glycerol derivatives of the invention are characterized by the formula

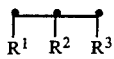
I wherein one of the residues $R^1$, $R^2$ and $R^3$ is a group U of the formula $OY^1$ or $-X^1-CO-(A^1)_n-Z^1$, another residue is a group V of the formula $OY^2$ or $-X^2-CO-(A^2)_p-Z^2$, and the remaining residue is a group W of the formula $-X^3T-(C_{2-6}\text{-alkylene})-N^+R\ A^-$ in which one of $X^1$, $X^2$ and $X^3$ is oxygen or a group $NQ^1$ and the other two are oxygen.

$Y^1$ is $C_{10-26}$-alkyl or $C_{10-26}$-alkenyl, $Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl, $A^1$ and $A^2$ are oxygen or a group $NQ^2$, n and p are the integer 1 or 0, $Z^1$ is $C_{9-25}$-alkyl or $C_{9-25}$-alkenyl, $Z^2$ is $C_{1-5}$-alkyl, $C_{2-5}$-alkenyl, phenyl or, when $A^2$ is not oxygen, $Z^2$ is also hydrogen, T is carbonyl, COO or $CONQ^3$ or, when $X^3$ is oxygen, T is also methylene, $Q^1$, $Q^2$ Q and $Q^3$ are hydrogen, $C_{1-4}$-alkyl.

$C_{3-6}$-cycloalkyl or phenyl, $A^-$ is the anion of a strong acid, $-N^+R$ is a group $-N^+(Y^3, Y^4, Y^5)$ or, when at least one of $X^1$, $X^2$, $X^3$, $A^1$, $A^2$ and T contains a substituted N-atom, $-N^+R$ is also a 5- or 6-membered aromatic group attached to the quaternary nitrogen, optionally with an additional hetero atom O, S or N, optionally with fused benzene and optionally mono-substituted by alkyl or alkoxy with up to 4 C-atoms, hydroxy, nitro, carbamoyl or ureido, $Y^3$ and $Y^4$ are $C_{1-6}$-alkyl or taken together are $C_{3-6}$-alkylene, and Y is $C_{1-6}$-alkyl, with the proviso that $R^2$ contains the group OCOO or a substituted N-atom when simultaneously $R^1$ is a group $OY^1$ or $OY^2$ and $R^3$ is a group W in which $X^3$ is oxygen and T is methylene or carbonyl, and their hydrates.

DETAILED DESCRIPTION OF THE INVENTION

The glycerol derivatives of the invention are characterized by the formula

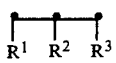
I wherein one of the residues $R^1$, $R^2$ and $R^3$ is a group U of the formula $OY^1$ or $-X^1-CO-(A^1)_n-Z^1$, another residue is a group V of the formula $OY^2$ or $-X^2-CO-(A^2)_p-Z^2$, and the remaining residue is a group W of the formula $-X^3T-(C_{2-6}\text{-alkylene})-N^+R\ A^-$ in which one of $X^1$, $X^2$ and is oxygen or a group $NQ^1$ and the other two are oxygen, $Y^1$ is $C_{10-26}$-alkyl or $C_{10-26}$-alkenyl, $Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl, $A^1$ and $A^2$ are oxygen or a group $NQ^2$, n and p are the integer 1 or 0, $Z^1$ is $C_{9-25}$-alkyl or $C_{9-25}$-alkenyl, $Z^2$ is $C_{1-5}$-alkyl. $C_{2-5}$-alkenyl, phenyl or, when $A^2$ is not oxygen. $Z^2$ is also hydrogen, T is carbonyl, COO or $CONQ^3$ or, when $X^3$ is oxygen, T is also methylene, $Q^1$, $Q^2$ and $Q^3$ are hydrogen, $C_{1-4}$-alkyl, $C_{3-6}$-cycloalkyl or phenyl, $A^-$ is the anion of a strong acid, $-N^+R$ is a group $-N^+(Y^3,Y^4,Y^5)$ or, when at least one of $X^1$, $X^2$, $X^3$, $A^1$, $A^2$ and T contains a substituted N-atom, $-N^+R$ is also a 5- or 6-membered aromatic group attached to the quaternary nitrogen, optionally with an additional hetero atom O, S or N optionally with fused benzene and optionally mono-substituted by alkyl or alkoxy with up to 4 C-atoms, hydroxy, nitro, carbamoyl or ureido $Y^3$ and $Y^4$ are $C_{1-6}$-alkyl or taken together are $C_{3-6}$-alkylene, and $Y^5$ is $C_{1-6}$-alkyl, with the proviso that $R^2$ contains the group OCOO or a substituted N-atom when simultaneously $R^1$ is a group $OY^1$ or $OY^2$ and $R^3$ is a group W in which $X^3$ is oxygen and T is methylene or carbonyl their hydrates. and terms "alkyl" and "alkenyl" used herein denote The straight-chain or branched, saturated and mono-unsaturated residues, respectively such as methyl, ethyl, propyl, isopropyl, 2-propenyl, butyl, isobutyl hexadecyl, heptadecyl, octadecyl and octadecenyl, especially methyl and octadecyl. Examples of $C_{3-6}$-cycloalkyl residues are cyclopropyl and cyclohexyl, examples of $C_{5-6}$-cyclo-alkenyl residues are 2-cyclopentenyl and especially 2-cyclohexyl, $C_{2-6}$-alkylene groups can be straight-chain or branched. Examples thereof are n-butylene, 2-methylpropylene; preferably ethylene and propylene. Examples of residues $-N^+(Y^3,Y^5,Y^5)$ are 1-methylpiperidinium and trimethylammonium. Examples of heterocyclic groups $N^+R$ are oxazolium isoxazolium, pyridinium, pyridazinium, quinolinium isoguinolinium; preferably N-methylimidazolium and thiazolium.

Examples of anions of strong organic or inorganic acids are $C_{1-4}$-alkylsulfonyloxy, phenylsulfonyloxy, tosyloxy, camphor-10-sulfonyloxy or $Cl^{31}$, $Br^-$, $I^-$, $ClO_4^-$, $SO_4^{--}$, $PO_4^{---}$ and $NO_3^-$.

The compounds of formula I can be hydrated. The hydration can take place in the course of the manufacturing process or can occur gradually as a result of hygroscopic properties of an initially anhydrous compound of formula I.

The compounds of formula I contain at least one asymmetric C-atom and can accordingly exist as optically active enantiomers, as diastereomers or as mixtures thereof, for example, as racemates.

Preferred compounds of formula I are those in which $R^1$ is a group U, $R^2$ is a group V and $R^3$ is a group W.

Still more preferred compounds of formula I are those in which $R^1$ is octadecanoyloxy, octadecylcarbamoyloxy, octadecyloxy, octadecyloxyformamido, N-isopropyloctadecyloxyformamido or 1-isopropyl-3-octadecylureido and/or $R^2$ is acetamido, methoxyformamido, methoxy, methyl- carbamoyloxy or methoxycarbonyloxy and/or $R^3$ is [4-(tri-methylammonio)-n-butyryloxy]chloride, [2-(1-methylpiperidinio)ethoxycarbonyloxy]chloride, [4-(3-thiazolio)-n- -butoxy]bromide, [4-(trimethylammonio)-n-butoxy]bromide or [4-(3-methyl-imidazolio)-n-butoxy]bromide.

The compounds of formula I and their hydrates can be prepared by a) reacting a compound of the formula

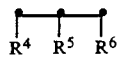   II wherein the residues $R^4$, $R^5$ and $R^6$ have the same significance as the residues $R^1$, $R^2$ and $R^3$, respectively, but with the proviso that a leaving group is present in group W in place of the residue $-N^+R\ A^-$,
with an amine of the formula NR, corresponding to the group $-N^+R$ as previously described, or b) reacting a compound of the formula

   II wherein the residues $R^7$, $R^8$ and $R^9$ have the same significance as the residues $R^1$, $R^2$ and $R^3$, respectively, but with the proviso that a hydroxy group or an amino group is present in place of one of the groups U and V, with an acid of the formula $$Z^1-(A^1)_n-COOH\ \text{IVa or}\ Z^2-(A^2)_p-COOH \quad \text{IVb}$$

or a reactive derivative thereof, or with an isocyanate of the formula
$Z^1NCO$ Va or $Z^2NCO$ Vb or an imidazolide of the formula

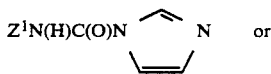  VIa or

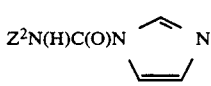  VIb or c) reacting a compound of the formula

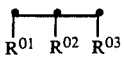  VII wherein $R^{01}$, $R^{02}$ and $R^{03}$ and have the same significance as the residues $R^1$, $R^2$ and $R^3$, respectively, but with the proviso that a group $-N(Y^3,Y^4)$ is present in group W in place of the group $-N^+R\ A^-$,
with a $C_{1-6}$-alkyl halide, wherein $R^1$, $R^2$, $R^3$, $-N^+R$, $A^-$, U, V, W, $Z^1$, $Z^2$, $A^1$, $A^2$, $Y^3$, $Y^4$, n and p are as previously described.

Examples of leaving groups present in the compounds of formula II are chlorine, bromine, iodine, mesyloxy, phenylsulfonyloxy and tosyloxy. The reaction of a compound II with an amine NR can be carried out in a known manner, for example, at a temperature up to the reflux temperature of the reaction mixture conveniently at about 80° C., optionally in a solvent such as acetonitrile, nitromethane or an aromatic hydrocarbon, for example toluene or benzene, or in tetrahydrofuran.

Examples of reactive derivatives of the acids of formula IVa or IVb are acid bromides or acid chlorides and anhydrides. The reaction of such an acid or of one of its reactive derivatives with a compound of formula III can be carried out in a known manner. An acid chloride or acid bromide can be reacted with the compound III in the presence of a base at a temperature of about 0 to 80° C. An anhydride can be reacted with the compound III in the presence of a catalyst such as dimethylaminopyridine, conveniently in a solvent. Halogenated hydrocarbons such as chloroform or dichloroethane can be used as solvents and organic bases such as triethylamine, quinoline or pyridine or inorganic bases such as alkali or alkaline earth metal hydroxides, carbonates or bicarbonates, for example, sodium carbonate, potassium bicarbonate and calcium carbonate, can be used as bases.

The reaction of a compound of formula III with an isocyanate of formula Va and Vb or with a corresponding imidazolide of formula VIa or VIb can be carried out in a solvent such as chloroform, acetone or dimethylformamide at a temperature between about 0 and 100° C, preferably at about 40-60° C. conveniently in the presence of a catalyst such as a Lewis base for example, triethylamine or diisopropylethylamine. If desired the reaction can also be carried out without the addition of a solvent.

The reaction of an amine of formula VII with a $C_{1-6}$-alkyl halide can be carried out in a known manner, for example, in a solvent such as dichloromethane or chloroform, at a temperature between room temperature and 50° C. preferably at room temperature. The iodide form is preferably used as the halide.

The compounds of formula II can be prepared from compounds of formula IX or X and the compounds of formula III can be prepared from compounds of formula VIII according to the following Reaction Scheme:

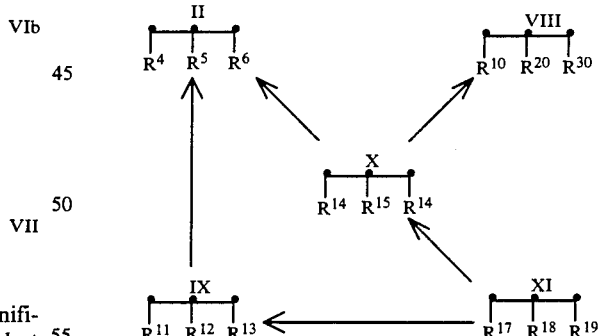

In the compounds of formula VIII the residues $R^{10}$, $R^{20}$ and $R^{30}$ have the same significance as the residues $R^1$, $R^2$ and $R^3$, but with the proviso that an optionally protected hydroxy or amino group or an azido group is present in place of one of the groups U and V.

In the compounds of formula IX the residues $R^{11}$, $R^{12}$ and $R^{13}$ and have the same significance as the residues $R^1$, $R^2$ and $R^3$, but with the proviso that an optionally protected hydroxy or amino group or an azido group is present in place of the group W.

In the compounds of formula X one of the residues $R^{14}$, $R^{15}$ and $R^{16}$ is an optionally protected hydroxy or amino group or an azido group, another residue is a group U or V and the remaining residue is a group W in which a leaving group is present in place of —N+R A⁻.

In the compounds of formula XI one of the residues $R^{17}$, $R^{18}$ $R^{19}$ is an optionally protected hydroxy or amino group or an azido group, another residue is an optionally protected hydroxy group, and the remaining residue is a group U or V.

Examples of protected hydroxy and amino groups are ether groups such as benzyloxy, trityloxy or 2-tetrahydropyranyloxy, and succinimide, phthalimide, benzyloxycarbonylamino or t-butoxycarbonylamino, respectively.

For the preparation of a compound of formula II, a compound of formula IX in which, for example, $R^{13}$ is hydroxy can be reacted with a halide of the formula Hal-T-($C_{2\text{-}6}$-alkylene)-G, wherein G is a leaving group, Hal is a halogen atom and T is as previously described, in the presence of a base such as pyridine or with an isocyanate of the formula O=C=N—($C_{2\text{-}6}$-alkylene)-G.

Alternatively, a compound of formula X in which for example, $R^{14}$ is hydroxy can be converted into the corresponding compound of formula II in which $R^4$ is a group U or V, which can be carried cut in the same manner as the conversion of a compound III into a compound I described above.

Analogously, a compound of formula XI in which for example. $R^{17}$ is hydroxy and $R^{19}$ is a protected hydroxy or amino can be converted into the corresponding compound of formula IX in which $R^{11}$ is a group U or V.

An azido group or a protected hydroxy or amino group, for example, $R^{13}$ present in a compound of formula IX can be converted into the free hydroxy or amino group in a known manner. A benzyl group can be cleaved by hydrogenolysis, for example, over palladium, a trityl group can be cleaved by means of trifluoroacetic acid or dilute hydrochloric acid and a 2-tetrahydropyranyl group can be cleaved by means of dilute acid. An azido group can be converted into the amino group with a complex metal hydride such as lithium aluminum hydride or by means of hydrogen/-Palladium carbon. Analogously, an azido group or a protected hydroxy or amino group present in a compound formula VIII, X or XI can be converted into the free hydroxy or amino group, In this manner, a compound of formula VIII in which, for example, $R^{10}$ is a protected hydroxy or amino group is converted into the corresponding compound of formula III in which $R^7$ is hydroxy.

For the preparation of a compound of formula X wherein, for example, $R^{16}$ is a group W in which a leaving group is present in place of —NR+A⁻, the corresponding compound of formula XI in which $R^{19}$ is hydroxy can be treated in the same manner as described above for the conversion of a compound IX into a compound of formula II.

The conversion of a compound of formula X into a compound of formula VIII can be carried out in the same manner as the conversion of a compound II into a compound I.

A compound of formula VII can be prepared starting from the corresponding compound of formula IX in which the residues $R^{11}$, $R^{12}$ and $R^{13}$ have the same significance as the residues $R^1$, $R^2$ and $R^3$, but with the proviso that a hydroxy or amino group is present in place of the group W.

Thus, a compound of formula IX in which, for example, $R^{13}$ is hydroxy can be reacted in a solvent such as dichloromethane with phosgene in toluene and subsequently with an alcohol of the formula HO—($C_{2\text{-}6}$-alkylene)—N($Y^3$, $Y^4$), wherein $Y^3$ and $Y^4$ have the above significance, for example, with 1-(2-hydroxyethyl)-piperidine, to give the corresponding compound of formula VII in which the residue $X^3T$ in the group W is a OCOO grouping.

The compounds of formula II in which one of the residues $R^4$, $R^5$ and $R^6$ contains an amino group $X^1$, $X^2$ or $X^3$ can also be prepared starting from a compound of the formula

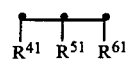 XII wherein one of the residues $R^{41}$, $R^{51}$ and $R^{61}$ is a group N(H,Q), another residue is, for example, a group O—($C_{2\text{-}6}$-alkylene)—G', wherein Q has the same significance as $Q^1$, $Q^2$ or $Q^3$ and G' is a protected hydroxy group such as trityloxy or benzyloxy. The preparation of the compounds XII and their conversion into compounds of formula II can be carried out in a known manner, for example, as described in Examples 5A and 7A.

The compounds of formulas II, III and VIII also form part of the invention.

The compounds of formula I and their hydrates inhibit blood platelet activating factor (PAF) and can accordingly be used in the control or prevention of illnesses such as thrombosis, apoplexy, heart infarct, angina pectoris, high blood pressure and bronchial asthma caused by allergy, and as well as antiinflammatories and antirheumatics. Further, the compounds of formula I and their hydrates have an inhibitory activity on the growth of tumor cells and can accordingly be used as antitumor agents.

The inhibitory on PAF can e demonstrated as follows:

Platelet-rich plasma (pRp) is prepared by centrifugation of rabbit blood containing 1/10 volumes of 90 mM trisodium citrate. The aggregation of the blood platelets is measured with the aid of an aggregometer at 37° C. while stirring. 2 minutes after the addition of the test substance to the PRP the platelet aggregation is triggered off by a sub-maximum dosage of PAF (4 nM). The $IC_{50}$ value ($\mu$M) given in the following Table corresponds to that concentration of the test substance which reduces to a half the aggregation of the blood platelets brought about by PAF.

| | Product of Example: | | | | | | | | |
|---|---|---|---|---|---|---|---|---|---|
| | 1 | 2 | 3 | 4 | 5 | 6 | 7 | 8 | 9 |
| $IC_{50}$ ($\mu$M) | 5.5 | 1.8 | 4 | 1.8 | 0.04 | 0.5 | 0.05 | 0.4 | 0.06 |

As mentioned earlier, medicaments containing a compound of formula I or a hydrate thereof are likewise an object of the present invention, as is a process for the preparation of such medicaments, which process comprises bringing one or more compounds of formula I or a hydrate thereof and, if desired, one or more other therapeutically valuable substances, into a galenical form.

The medicaments can be administered enterally, for example, orally in the form of tablets, coated tablets, dragees, hard and soft gelatine capsules, solutions, emulsions or suspensions, or rectally, for example, in the form of suppositories, or as a spray. The administration can, however, also be carried out parenterally, for example, in the form of injection solutions.

For the preparation of tablets, coated tablets, dragees and hard gelatine capsules, the active substance can be mixed with pharmaceutically inert, inorganic or organic excipients. As such excipients there can be used for tablets, dragees and hard gelatine capsules, for example, lactose, maize starch or derivatives thereof, talc, stearic acid or its salts. For soft gelatine capsules, suitable as excipients are, for example, vegetable oils, waxes, fats, semi-solid and liquid polyols; depending on the nature of the active substance no excipients are, however, generally required in the case of soft gelatine capsules. For the preparation of solutions and syrups, suitable as excipients are, for example, water, polyols, saccharose, invert sugar and glucose. For injection solutions suitable as excipients are, for example, water, alcohols polyols, glycerine and vegetable oils. For suppositories, suitable as excipients are, for example, natural or hardened oils waxes, fats and semi-liquid or liquid polyols The pharmaceutical preparations can contain, in addition, preservatives, solublizers, stabilizing agents. wetting agents, emulsifying agents, sweetening agents, coloring agents, flavoring agents, salts for varying the osmotic pressure, buffers, coating agents or antioxidants.

The dosage of the active substance can vary within wide limits and is, of course, fitted to the individual requirements in each particular case. In general in the case of oral administration a dosage of about 0.1 to 20 mg/kg, preferably of about 0.5 to 4 mg/kg, per day can be appropriate, although the upper limit just given can also be exceeded if this should be found to be indicated.

The examples which follow further illustrate the invention. The temperatures are in degrees Centigrade unless otherwise stated.

EXAMPLE 1

A. Preparation of the starting material a) 15.35 g of (RS)-1-O-benzyl-3-O-tritylglycerol (36.15 mmol) (Helv. Chim. Acta 65. 1982, 1059) were dissolved in 75 ml of chloroform. There were added thereto 10 ml of pyridine followed by 10.5 g of tosyl chloride. The chloroform was removed by distillation after 24 hours at room temperature. The residue was taken up in 50 ml of pyridine. 10 ml of water and then 10 g of potassium bicarbonate were added thereto. After distillation of the solvent the residue was taken up in toluene, the solid portion was separated, the organic phase was then shaken out with water, dried and evaporated. The product crystallized from the melt upon cooling, yield 95%, m.p. 98°–100° C.

b) The (RS)-1-0-benzyl-2-0-tosyl-3-0-tritylglycerol obtained was converted into (RS)-1-0-benzyl-2-deoxy-2-azido-3-0-tritylglycerol by means of sodium azide in dry dimethyl formamide while heating.

c) A solution of the azide obtained in dry diethyl ether was reduced by means of a suspension of lithium aluminum hydride in dry diethyl ether to give (RS)-1-O-benzyl-2-deoxy-2-amino-3-0-tritylglycerol, m.p. 67°–69° C.

d) A solution of the amine obtained in dioxane was converted with dilute hydrochloric acid into (RS)-1-O-benzyl-2-deoxy-2-aminoglycerol hydrochloride. m.p. 148°–149° C.

e) An aqueous solution of the hydrochloride obtained is made alkaline with a sodium hydroxide solution the liberated amine is taken up in methylene chloride and the solvent is removed.

f) 2 g of potassium carbonate in 3 ml of water were added to a solution of 1.6 g of the resulting (RS)-1-O-benzyl-2-deoxy-2-aminoglycerol (8.8 mmol) in 10 ml of dichloromethane. 2 ml of acetic anhydride were then added dropwise while stirring. After 1 hour, the reaction mixture was worked-up. For purification, the compound was chromatographed over silica gel with ether/methanol (9:1). There were obtained 1.4 g of (RS)-1-0-benzyl-2-deoxy-2-acetamidoglycerol as a liquid (81% of theory).

g) 2.1 g of stearoyl chloride in 5 ml of chloroform were added dropwise to a solution of 1.4 g of (RS)-1-O-benzyl-2-deoxy-2-acetamidoglycerol in 10 ml of chloroform and 1.5 ml of pyridine. After 1 hour at room temperature, the mixture was worked-up. For purification, the compound was chromatographed over silica gel with dichloromethane/ether (1:1). After crystallization from n-hexane, there were obtained 2.4 g of white crystals (78% of theory), m.p. 65°–66° C.

h) A solution of 1.5 g of the (RS)-1-0-stearoyl-2-deoxy-2-acetamido-3-0-benzylglycerol obtained in 20 ml of tetrahydrofuran was hydrogenated in the presence of 0.5 g of 10% pd-carbon under a slight hydrogen overpressure. The (RS)-1-O-deoxy-2-acetamidoglycerol was obtained in quantitative yield. m.p. 89°–90° C. (from n-hexane).

i) 0.4 g of 4-chlorobutyryl chloride (2.8 mmol) in 5 ml of chloroform was added dropwise in an ice-bath with the exclusion cf moisture to a solution of 1.1 g of (RS)-1-0-stearoyl-2-deoxy-2-acetamidoglycerol (2.75 mmol) in 20 ml of chloroform and 0.5 ml of triethylamine. The reaction mixture was stirred for 2 hours. After working-up, the (RS)-1-O-stearoyl-2-deoxy-2-acetamido-3 -0-(4-chlorobutyryl)glycerol was crystallized from n-hexane. There were obtained 1.39 g of white crystals (yield: quantitative). M.p. 51–°52° C.

B. Preparation of the product 0.45 g of (RS)-1-0-stearoyl-2-deoxy-2 -acetamido-3-O-(4-chlorobutyryl)glycerol was treated with 2 ml of a 20% solution of trimethylamine in acetonitrile and reacted in a bomb-tube at 80° C. for 24 hours. For purification, the compound was chromatographed on silica gel with chloroform/methanol (7:3). There was obtained 0.22 g of [3-[[(RS)-2-acetamido-3-[octadecanoyloxy]propoxy]carbonyl]propyl]trimethylammonium chloride (yield: 44% of theory). m.p. 205° C.

EXAMPLE 2

A. Preparation of the starting material a) A solution of 450 mg of (RS)-I-0-benzyl-2-deoxy-2-aminoglycerol hydrochloride in methanol was treated with a solution o-f potassium hydroxide in water. The methanol was removed by distillation. Water and dichloromethane were added to the residue and the mixture was treated with methyl chloroformate. There were obtained 470 mg (95%) of (RS)-1-deoxy-2-(1-methoxyformamido)glycerol as an oil.

b) 0.45 g of (RS)-1-O-benzyl-2-deoxy-2-(1-methoxyformamido)glycerol (1.88 mmol) was treated with 0.6 g of octadecyl isocyanate and the solution was heated to 90° C. for 1 hour. It was chromatographed on silica gel with a mixture of toluene and ethyl acetate,.(4:1). After crystallization from n-hexane, there was obtained 0.65 g of (RS)-1-O-benzyl-2-deoxy-2-(1-methoxyformamido)-3-0-(octadecylcarbamoyl)glycerol, m.p. 65°–67 c) 4.9 g of (RS)1-O-benzyl-2-deoxy-2-(1-methoxy formamido)-3-O-(octadecylglycerol in 75 ml of tetrahydrofuran were hydrogenated in the presence of 1 g of 10% Pd-carbon at a slight hydrogen overpressure. There were obtained 4.05 g of (RS)-2-deoxy-2-(1-methoxyformamido)-1-O-octadecylcarbamoylglycerol, m.p. 86° C. (from n-hexane).

d) 0.75 ml of 4-chlorobutyryl chloride (6.68 mmol) in 5 ml of chloroform was added dropwise on an ice-bath with the exclusion of moisture to a solution of 2 g of (RS)-2-deoxy-2-(1-methoxyformamido)-1-O-octadecylcarbamoylglycerol (4.5 mmol) in 20 ml of chloroform and 0.7 ml of triethylamine. The reaction mixture was stirred at room temperature for 2 hours. After working-up, the reaction product was filtered on silica gel with dichloromethane/ether (1:1). There were obtained 2.3 g of (RS)-1-O-(4-chlorobutyryl)-2-deoxy-2-(1-methoxyformamido)-3-O-(octadecylcarbamoyl)glycerol after crystallization from n-hexane, m.p. 68°-70° C.

B. Preparation of the product

Analogously to Example 1B, from 0.4 g of the chloride obtained under A.d) there was prepared 0.31 g (70%) of [3-[[(RS)-2-(1-methoxyformamido)-3-(octadecylcarbamoyloxy)propoxy] carbonyl]propyl]trimethylammonium chloride, m.p. 200° C. (dec.).

EXAMPLE 3

A. Preparation of the starting material

A solution of 500 mg (1.4 mmol) of (RS)-2-O-methyl-1-O-octadecylglycerol in 5 ml of dichloromethane was treated at 0° C. with 2 ml (4 mmol) of a 20% solution of phosgene in toluene. The mixture was then stirred without cooling for 3 hours.. The excess phosgene and dichloromethane were removed. Then, a solution of 500 mg (3.9 mmol) of 1-(2-hydroxyethyl)-piperidine in 10 ml of dichloromethane was reacted. After stirring for 2 hours, the solvent was evaporated. The residue was chromatographed on silica gel. By elution with toluene-ethyl acetate (1:1) and then with ethyl acetate, there was obtained (RS)-2-0-methyl-1-0-octadecyl-3-O-[[2-(1-piperidino)ethoxy] carbonyl]glycerol, m.p 34° C.

B. Preparation of the product

A solution of 100 mg (0.195 mmol) of the product obtained under 3A. in 5 ml of dichloromethane was treated with 100 mg (0.7 mmol) of methyl iodide and the mixture was left to stand at room temperature for 3 days. The solvent was evaporated and the residue was percolated over a chloride-loaded anion exchange resin with methanol-dichloromethane (4:1). The solvent was evaporated and the residue was chromatographed on silica gel. Elution with chloroform-methanol-Water (60:35:5) gave 1-[2-[[[(RS)-2-methoxy-3-(octadecyloxy)propoxy]carbonyl]oxy]ethyl]-1-methylpiperidinium chloride, m.p. 59° C.

EXAMPLE 1

A. preparation of the starting material a) An aqueous potassium hydroxide solution was added to a solution of 0 9 g of (RS)-1-deoxy-1-amino-3-0benzylglycerol (5 mmol) in 20 ml of dichloromethane. A solution of 1.7 g of octadecyl chloroformate in 10 ml of dichloromethane was added dropwise to the mixture while stirring. After stirring for 1 hour at room temperature, the mixture was worked-up and the compound obtained was chromatographed on silica gel with n-hexane/ether.(1:1). After crystallization from n-hexane, there were obtained 1.6 g of crystals, m.p. 58°-69° C.

b) 2 g of (RS)-1-0-benzyl-3-deoxy-3-[1-(octadecyloxy)formamido]glycerol were heated to 40° C. for 2 hours with 2 ml of methyl isocyanate and 0.5 ml of triethylamine. After removing the excess reagent, the product was recrystallized from n-hexane and there were thus obtained 2 g (89.3%) of (RS)-1-0-benzyl-3-deoxy-3-[1-(octadecyloxy)formamido]-2-0-methylcarbamoylglycerol, m.p. 95-96.5° C.

c) (RS)-1-0-(4-Chlorobutyryl)-3-deoxy-3-[1-(octadecyloxy)formamido]-2-0-methylcarbamoylglycerol was prepared via (RS)-3-deoxy-3-[1-(octadecyloxy)formamido]-2-0-methylcarbamoylglycerol analogously to Example 1A.h) and i).

B. Preparation of the product

[3-[[(RS)-2-Methylcarbamoyloxy-3-[1-(octadecyloxy)-formamido]propoxy]carbonyl]propyl]trimethylammonium chloride, m.p. >200° C. was prepared analogously to Example 1B.

EXAMPLE 5

A. Preparation of the starting material a) 5 ml of epichlorohydrin were added dropwise while cooling with an ice-bath to 30 ml of 1.4-butanediol and 0.2 ml of BF$_3$. Et$_2$O. The mixture was left to react at room temperature overnight. The excess butanediol was firstly distilled and then 10 g (85%) of RS-1-chloro-1-deoxy-3-0-(4-hydroxybutyl)glycerol were distilled as a colorless liguid, b.p.: 110° C/0 1 mm Hg; IR (cm-$^{-1}$): 3360 (OH); 1124 (ether); 1058 (alcohol-II bands).

b) The diol of a) was reacted with trityl chloride in pyridine. There was obtained RS-1-chloro-1-deoxy-3-0-[4-(trityloxy)butyl]glycerol as a viscous liguid. IR (cm-$^{-1}$) 3554 (OH); 1596 and 1490 (aromatic); 1120 (ether): 1072 and 1032 (alcohol): 764, 746. 706 (monosubst. benzene).

c) For the preparation of 1.2-epoxy-3-[4-(trityloxy)-butoxy]propane, 4.85 g of the product of b) were dissolved in 20 1 of tetrahydrofuran and reacted under reflux with 2 g of potassium t-butylate. The product was obtained in quantitative Yield, IR (cm-$^{-1}$) 1596 and 1490 (aromatic); 1090 and 1073 (ether); 764, 747 and 706 (monosubst. benzene).

d) The reaction cf the epoxide of c) with isopropylamine in a pressure flask at 70° C. for 8 hours gave (RS)-3-deoxy-3-(isopropylamino)-1-0-[4-(trityloxy)butyl]-glycerol in quantitative yield, IR (cm-1) 3380 and 3301 (OH and NH); 1597 and 1490 (aromatic); 1123 and 1074 (ether); 764, 746 and 706 (monosubst. benzene).

e) 2.4 q of the amine of d) and 2 g of octadecyl chloroformate in 20 ml of dichloromethane were stirred at room temperature for 1 hour, in the presence of 2 ml of 30% potassium hydroxide solution. The product was chromatographed on silica gel with ether-chloroform-pyridine (49.5:49.5:1). There were obtained 3.1 g (78%) of a colorless liguid. IR (cm$^{-1}$): 3421 (OH); 1696, 1669 and 1489 (aromatic); 1206 (ester): 1124 and 1074 (ether); 774. 764, 745 and 705 (monosubst. benzene).

f) The reaction of the product of e)-with methyl isocyanate gave (RS)-1-deoxy-1-[N-isopropyl-1 -(octadecyloxy)-formamido]-2-0 -(methylcarbamoyl)-3-0-[4-(trityloxy)-butyl]glycerol as a colorless liquid.

g) The product of f) was reacted with aqueous hydrochloric acid in dioxan at 95° C. Chromatography on silica gel with ethylacetate gave (RS)-1-deoxy-1-[N-isopropyl-1-(octadecyloxy)formamido]-3-0-(4-hydroxybutyl)-2-0-(methylcarbamoyl)glycerol as a colorless liquid IR (cm-1): 3353 and 3058 (NH and OH); 1702 (carbamate); 1539 (amide); 1255 (ester), 1120, 1095 and 1071 (alcohol and ether).

h) The product of g) was brominated with triphenylphosphine dibromide in the presence of triethylamine (stochiometric amounts). From 1.2 g of starting material there was obtained after chromatography on silica gel with toluene-ethylacetate (1:1), 0.9 g (67%) of bromide as a colorless liquid, IR (cm.$-^1$) 3356 (NH); 1702 (carbamate): 1530 (amide); 1251 (NH-CO); 1132 (ether).

B. Preparation of the product 0.3 g of (RS)-1-0-(4-bromobutyl)-3-deoxy-3-[N-isopropyl-3-(octacecyloxy)formamido]-2 -0-(methylcarbamoyl)glycerol was treated with 0.3 ml of thiazole and the reaction mixture was held at 80° C. for 5 hours. After removal of the excess reagent by distillation the compound was purified on silica gel with chloroform/methanol (7:3). There was obtained 0.17 g (50%) of 3-[4-[(RS)-3-[N-isopropyl-1-(octadecyloxy)formamido]- 2-[(methylcarbamoyl)oxy]-propoxy]butyl]-thiazolium bromide, MS: m/e=626 (M+ of the cation).

EXAMPLE 6

0.4 g of the same starting material as in Example 5 was dissolved in 3 ml of tetrahydrofuran and treated with 2 ml of a 20% triethylamine solution in tetrahydrofuran. The mixture was left to react at 80° C. for 2 hrs. in a pressure flask. For purification, filtration was carried out over silica gel with chloroform-methanol (1:1). There was obtained 0.42 g (96%) of [4-[(RS)-3-[N-isopropyl-(1-octadecyloxy)formamido]-2-[(methylcarbamoyl)oxy]propoxy]butyl]trimethylammonium bromide, MS: m/e=600 (M+ of the cation).

EXAMPLE 7

A. Preparation of the starting material a) Analogously to Example 5A.a). from epichlorohydrin and 4-benzyloxy-1-butanol there was obtained (RS)-1-0-[4-(benzyloxy)butyl]-3-chloro-3-deoxyglycerol as a colorless liquid.

b) 15 g of the product of a) were taken up in 20 ml of isopropylamine and reached at 80° C. for 6 hours, in a pressure flask. The excess isopropylamine was then removed by distillation. The hydrochloride formed was precipitated with ether and discarded. There was obtained (RS)-1-0-[4-(benzyloxy)butyl]-3-deoxy-3-(isopropylamino)glycerol, IR (cm$^{-1}$): 3302 (OH and NH); 1496 (aromatic); 1103 (,ether and alcohol-II bands); 737 and 698 (monosubst. benzene).

c) an organic phase consisting of 20 ml of dichloromethane, 5.9 g of the product of b) and 6.65 g of octadecylcarbamidoyl chloride was stirred for 2 hours with 5 ml of 30% potassium hydroxide solution. After chromatography on silica gel with chloroform-ethylacetate-toluene (1:1:1) there were obtained 7.9 g (67%) of (RS)-3-O-[4-benzyloxy)butyl[-1-deoxy-1-(1-isopropyl-3-octadecylureido)glycerol, MS (m/e): 72 (100%;=NHCH(CH$_3$)$_2$; 296 (2%; O=CNH—C$_{18}$H$_{37}$).

d) 3 ml of methyl isocyanate were added to a solution of 3 g of the product of c) in 5 ml of dichloromethane and 0.5 ml of triethylamine. The mixture was left to react at 40° C. for 5 hours. The product was purified on silica gel with toluene-ethylacetate (1:1). There were obtained 2.5 g (76%) of a wax-like compound. IR (cm$^{-1}$): 3340 (NH); 1707 (carbamate); 1634 (urea); 1541 (amide-II bands); 1101 (ether); 735, 697 (monosubstituted benzene).

e) The catalytic hydrogenation of the product of d) over 10% palladium/carbon in tetrahydrofuran gave (RS)-1-deoxy-3-O-(4-hydroxybutyl)-1-(1-isopropyl-3-octadecylureido-2-O-(methylcarbamoyl)glycerol in quantitative yield, MS (m/e): 483 (100%; M-CH$_3$NHCOO); 558 (25%; M+H+).

f) The bromination of the product of e) was carried out analogously to Example 5A.h). IR (cm$^{-1}$); 3335 (NH); 2916 and 2849 (aliph. CH); 1694 (carbamate); 1623 (urea); 1556 and 1525 (amide-II bands and CO-NH open).

B. Preparation of the product 0.17 g (50%) of 3-[4-[(RS)-3-(1-isopropyl-3-octadecylureido)- 2-[(methylcarbamoyl)oxy]propoxy]-butyl]-thiazolium bromide MS (m/e): 625 (M+of the cation). was obtained from 0.3 g of (RS)-3-0-(4-bromobutyl)-1-deoxy-1-(1-isopropyl-3-octadecylureido)-2-0-(methylcarbamoyl)glycerol and thiazole analogously to Example 5 B.

EXAMPLE 8

0.2 g of the same starting material as in Example 7 was taken up in 0.5 ml of N-methylimidazole. The mixture was left to react at 80° C. for 30 minutes. After distilling the excess reagent, the compound was crystallized from methanol-ether. There was obtained 0.2 g (88%) of 1-[4-[(RS)-3-(1-isopropyl-3-octadecylureido)-2-[(methylcarbamoyl)oxy]propoxy]butyl]-3-methylimidazolium bromide, MS (m/e): 622 (M+ of the cation).

EXAMPLE 9

A. Preparation of the starting material a) A mixture of 6 g (20 mmol) of (RS)-1-0-(4-benzyloxybutyl)-3-deoxy-3-isopropylaminoglycerol and 6 66 g of octadecyl chloroformate in 50 ml of dichloromethane was stirred with 20 ml of 30g potassium hydroxide solution for 2 hours. After isolation of the product from the organic phase and chromatography on silica gel with toluene-ethyl acetate (4:1), there were obtained 11 g (91.5%) of (RS)-1-0-(4-benzyloxybutyl)-3-deoxy-3-(N-isopropyl-1-octadecyloxyformamido)-glycerol, IR (cm-1) 3431 (OH), 1696 and 1670 (carbamate), III9 (ether and alcohol-II bands); 734 and 697 (monosubst. benzene).

b) 4.5 g of the product from a) were esterified with methyl chloroformate in the presence of pyridine to give 3.8 g (80%) of (RS)-1-O-(4-benzyloxybutyl)-3-deoxy-2-methoxycarbonyl-3-(N-isopropyl-1-octadecyloxyformamido)glycerol, IR (cm ): 1751 (carbonate C=0), 1701 (carbamate C=0), 1266 (ester) 1101 (ether); 734 and 697 (monosubst. benzene).

c) 3.65 g of the product from b) were hydrogenated over 10% palladium/carbon in tetrahydrofuran to give 3.1 g (94%) of (RS)-1-deoxy-3-0-(4-hydroxybutyl)-1-(N-isopropyl-1-octadecyloxyformamido)-2-0-methoxycarbonylglycerol, m.p. 28° C.

d) Analogously to Example 5A.h., 2.9 g of the product of c) were brominated to give 2.5 g (77.5%) of (RS)-1-0-(4-bromobutyl)-3-deoxy-3-(N-isopropyl-1-octadecyloxyformamido)-2-0-methoxycarbonyl-glycerol, IR (cm.$^{-1}$) 1751 (carbonate CO), 1700 (carbamate CO), 1266 (ester), OH bands missing.

B. Preparation of the product

Analogously to Example 5B, 1.5 g of the product of A.d were reacted with 1 ml of thiazole to give 1.45 g (85%) of 3-[4-(RS)-3-(N-isopropyl-1-octadecyloxyformamido)-2-(methoxycarbonyloxy)propoxy]butyl]-thiazolium bromide 30 ml of ether)

EXAMPLE A

A compound of formula I can be used in a known manner as the active substance for the preparation of tablets of the following composition:

|  | Per tablet |
|---|---|
| Active substance | 200 mg |
| Microcrystalline cellulose | 155 mg |
| Maize starch | 25 mg |
| Talc | 25 mg |
| Hydroxypropylmethylcellulose | 20 mg |
|  | 425 mg |

EXAMPLE B

A compound of formula I can be used in a known manner as the active substance for the preparation of capsules of the following composition:

|  | Per capsule |
|---|---|
| Active substance | 100.0 mg |
| Maize starch | 20.0 mg |
| Lactose | 95.0 mg |
| Talc | 4.5 mg |
| Magnesium stearate | 0.5 mg |
|  | 220.0 mg |

We claim:

1. A method of inhibiting blood platelet activating factor which comprises administering to a host requiring such treatment an effective amount of a compound of the formula:

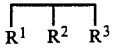

wherein $R^1$ is —OCO—$Z^1$, —OCOO—$Z^1$ or $NQ^1$ CO—$(A^1)_n$—$Z^1$, $R^2$ is $OY^2$ or —$X^2$—CO—$(A^2)_p$—$Z^2$; and $R^3$ is —$X^3$T—($C_{2-6}$-alkylene) —$N^{+R}$ $^{A-}$ in which one of $X^2$ and $X^3$ is oxygen and the other is oxygen, or if $R^1$ is —OCO—$Z^1$ or —OCOO—$Z^1$, one of $X^2$ and $X^3$ is also $NQ^1$;

$Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl, $A^1$ and $A^2$ are oxygen or a group $NQ^2$, n and p are the integer 1 or 0, $Z^1$ is $C_{9-25}$-alkyl or $C_{9-25}$-alkenyl, $Z^2$ is $C_{1-5}$-alkyl, $C_{2-5}$-alkenyl, phenyl or, when $A^2$ is not oxygen, $Z^2$ is also hydrogen, T is carbonyl, COO or $CONQ^3$ or, when $X^3$ is oxygen, T is also methylene, $Q^1$, $Q^2$ and $Q^3$ are hydrogen, $C_{1-4}$-alkyl, $C_{3-6}$-cycloalkenyl or phenyl, A$^-$ is the anion of a strong acid, —N+R is a 5- or 6-membered aromatic group attached to the quaternary nitrogen, optionally with an additional hetero atom O, S or N, optionally with fused benzene and optionally mono-substituted by alkyl or alkoxy with up to 4 C-atoms, hydroxy, nitro, carbamoyl or ureido, with the proviso that at least one of $R^1$, $R^2$ and $R^3$ contains a substituted N-atom, or its hydrate.

2. A method of inhibiting blood platelet activating factor, in accordance with claim 1, wherein $R^1$ is octadecanoyloxy, octadecyloxyformamido, N-isopropyloctadecyloxyformamido or 1-isopropyl-3-octadecylureido.

3. A method of inhibiting blood platelet activating factor, in accordance with claim 2, wherein $R^2$ is acetamido, methoxyformamido, methoxy, methylcarbamoyloxy or methoxycarbonyloxy.

4. A method of inhibiting blood platelet activating factor, in accordance with claim 3, wherein $R^3$ is [4-(trimethylammonio)-n-butyryloxy]chloride,

[2-(1-methylpiperidino)ethoxycarbonyloxy]chloride, [4-(3-thiazolio)-n-butoxy]bromide, [4-(trimethylammonio)-n-butoxy]bromide or [4-(3-methylimidazolio)-n-butoxy]bromide.

5. A method of inhibiting blood platelet activating factor, accordance with claim 1, wherein the compound of formula I is 3-[4-[(RS)-3-[N-isopropyl-1-(octadecyloxy)-formamido]-2-[(methylcarbamoyl) oxy]-propoxy]butyl)thiazolium bromide.

* * * * *

UNITED STATES PATENT AND TRADEMARK OFFICE
CERTIFICATE OF CORRECTION

PATENT NO. : 5,057,530

DATED : October 15, 1991

INVENTOR(S) : Richard Barner, Kaspar Burri, Jean-Marie Cassal, Paul Hadvary, Georges Hirth and Klaus Müller It is certified that error appears in the above-identified patent and that said Letters Patent is hereby corrected as shown below:

In Claim 1, Column 14, line 8, please delete "$-N^{+RA-}$" and insert therefor --- $-N^{+}R\ A^{-}$ --- .

Signed and Sealed this

Eighteenth Day of May, 1993

*Attest:*

MICHAEL K. KIRK

*Attesting Officer*     *Acting Commissioner of Patents and Trademarks*